United States Patent [19]

Thenard et al.

[11] Patent Number: 4,915,947

[45] Date of Patent: Apr. 10, 1990

[54] MICROENCAPSULATED FUNGICIDE

[75] Inventors: Jean Thenard, Paris, France; Shyam B. Advani, North Wales, Pa.

[73] Assignee: Pennwalt Corporation, Philadelphia, Pa.

[21] Appl. No.: 928,085

[22] Filed: Nov. 7, 1986

[51] Int. Cl.$^4$ .................. A01N 25/34; B01J 13/02
[52] U.S. Cl. ................... 424/408; 264/4.7; 428/402.21
[58] Field of Search ............ 264/4.7; 428/402.21; 424/408; 71/90, DIG. 1

[56]  References Cited

U.S. PATENT DOCUMENTS

| | | | |
|---|---|---|---|
| 3,577,515 | 5/1971 | Vandegaer | 264/4.7 X |
| 4,000,290 | 12/1976 | Itzerott | 514/367 |
| 4,155,741 | 5/1979 | Scher et al. | 71/DIG. 1 |
| 4,479,961 | 10/1984 | Martin | 514/367 |
| 4,640,709 | 2/1987 | Beestman | 428/402.21 X |

OTHER PUBLICATIONS

R. C. Koestler: "A Theory of Mechanism of Action of Encapsulated Herbicides and Insecticides", 3rd International Controlled Release Pesticide Symposium, Sep. 1976.

*Primary Examiner*—Richard D. Lovering

[57]  ABSTRACT

There are disclosed microcapsules containing a phytotoxic compound of the formula:

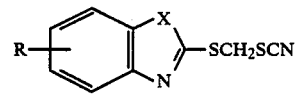

where x is oxygen or sulfur and R is alkyl, alkoxy, alkylamino, halo, nitro or hydrogen, and the microcapsule walls comprise resinous polycondensates which are crosslinked polyurea, crosslinked polyamide or crosslinked polyamide-polyurea wherein the degree of crosslinking is about 25–100%, the walls are about 10 to about 30% of the total weight of the microcapsules, and the microcapsules have an average size ranging from about 7 to about 25 microns in diameter.

17 Claims, No Drawings

MICROENCAPSULATED FUNGICIDE

BACKGROUND

This invention relates to a microencapsulated family of phytotoxic fungicides. More particularly, it relates to products which are phytotoxic fungicidal benzothiazole related compounds microencapsulated within walls of crosslinked polyamide, crosslinked polyurea or crosslinked polyamide-polyurea to provide an effective agent for direct foliar application to control fungal diseases on crops.

The microencapsulation of organophosphate insecticides has been previously used to upgrade characteristics that are lacking in these materials. Encasing the pesticide in an appropriate polymer shell increases residual by protecting it from substrate adsorption, vaporization and the general environment until such time as the target species contacts the capsule or else is exposed to vapors of active ingredient emanating from the capsule. Increased efficiency is obtained primarily by the concentrating effect of microencapsulation whereby the pesticide exists on the substrate in numerous point sources with much area between the capsules untreated. For example, when using capsules having an average size of 30 microns (μm) at the treatment level of 1 lb/acre, calculations show that greater than 99% of the area is not covered by capsules.

Because of the absence of microcapsules over such a large proportion of the area of treatment, it was reasoned by those skilled in the art[1], that the microencapsulation of fungicides would result in effects counter to those desired since proper usage of fungicides demands a maximum coverage of the treated area. In fact, there are presently no instances of commercial products which are microencapsulated fungicides.

[1] R. C. Koestler, "A Theory of Mechanism of Action of Encapsulated Herbicides and Insecticides", in 3rd International Controlled Release Pesticide Symposium, Sept. 1976

PRIOR ART

Microencapsulation by interfacial polycondensation is shown in various prior publications, for example, U.S. Pat. No. 3,577,515 which broadly teaches the encapsulation of pesticides and other active ingredients. A prior disclosure of the microencapsulation of the fungicide diphenyl is made in U.S. Pat. No. 3,607,776. However, the use of the microencapsulated diphenyl formulation is not intended for the foliar treatment of crops but for application to fruit in conjunction with ingestible microcapsules.

STATEMENT OF THE INVENTION

This invention is a fungicide product comprising microcapsules containing a phytotoxic compound of the formula:

where X is —O— or —S— and R is alkyl, alkoxy, alkylamino, halo, nitro or hydrogen wherein the alkyl group or alkyl radical has from 1 to 6 carbons, said microcapsules having walls of a resinous polycondensate selected from the group consisting of crosslinked polyurea, crosslinked polyamide and crosslinked polyamide-polyurea wherein the degree of crosslinking ranges from about 25 to 100%, said walls being about 10 to about 30% of the total weight of said microcapsules, and said microcapsules having an average size ranging from about 7 to about 25 microns in diameter.

DETAILED DESCRIPTION OF THE INVENTION

This invention concerns microcapsules having specified microcapsule walls encasing a member of a family of phytotoxic compounds of the type having the following structure:

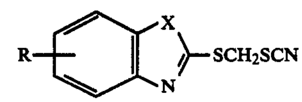

where X is —O— or —S— and R is alkyl, alkoxy, alkylamino, halo, nitro or hydrogen wherein the alkyl group and alkyl radicals have from 1 to 6 carbon atoms. These microcapsules may, in the form of suspensions, be applied to foliage to treat fungal diseases with minimal phytotoxic response. Thus, the proper selection of fungicide and microcapsule wall results in a product which has negligible phytotoxicity and may be applied to foliage at conventional rates with a high degree of efficacy.

In the preferred embodiment, the fungicide employed is 2-(thiocyanomethylthio) benzothiazole (TCMTB) where X in the above structure is —S— and R is H. In other embodiments, R is preferably methyl, ethyl, methoxy, chloro, bromo or hydrogen and X is sulfur.

These fungicides may be encapsulated neat or dissolved or emulsified in a water-immiscible solvent. Since the fungicides are generally solid at room temperature, they may be encapsulated neat by procedures carried out at elevated temperatures to maintain the fungicide in the liquid (melt) phase during the encapsulation process. Otherwise, solvents for the fungicide are used and will include, for example, xylene, methylene chloride, toluene, aromatic petroleum solvent, and other water immiscible solvents.

The amount of solvent used in solutions or emulsions with the benzothiazole fungicide is that amount sufficient to dissolve or suspend the active fungicide but below the amount which will substantially reduce the efficacy of the microencapsulated product. Preferably, the amount of solvent will range from about 5 to about 50% based on the combined weight of the active material and solvent.

MICROCAPSULE PREPARATION

In general, the microencapsulation procedure as used herein is described in U.S. Pat. No. 3,577,515 and involves interfacial condensation of the complementary, organic, polycondensate-forming intermediates reacting to form a crosslinked polyurea, polyamide or polyamide-polyurea resinous capsule wall about the fungicide or fungicide solution. The wall formulation is critical because too impervious a wall will not release the material, which will lead to decreased activity. A wall of too high a permeability will lead to premature loss of the active ingredient by adsorption and vaporization or loss through other environmental pathways.

The general procedure comprises (1) establishing by agitation, a dispersion of to-be-encapsulated droplets containing a first of said intermediates in a body of liquid which is (i) in continuous phase, (ii) immiscible with the droplets and (iii) essentially free of any reactant complementary to said first intermediate, and (2) thereafter bringing a second of said intermediates, i.e., complementary to the first intermediate, into the continuous liquid phase so that the first and second intermediates react at interfaces between the droplets and the continuous phase to encapsulate the droplets within a wall of said polycondensate.

To obtain crosslinking of the wall-forming polymer chains during the polycondensation reaction, at least one of said first and second intermediates comprises at least in part a polyfunctional reactant which (a) is complementary to the other of said intermediates and effective for crosslinking reaction and (b) has at least three reactive groups that are the same as each other and are preferably selected from the class consisting of amine, isocyanate, —COCl and SO$_2$Cl groups, said first and second intermediates thereby reacting to encapsulate the droplets within the aforesaid polycondensate wall having crosslinking therein. The degree of crosslinking of the polymer wall is critical in determining the reduction in phytotoxicity of the fungicide encased within the wall.

The percent of crosslinking, as reported herein, is that theoretically obtained when an amount of polyfunctional reactant is used to replace a given amount of difunctional reactant (percent crosslinking is based on 100% yield in the polycondensation reaction) However, the polycondensation reaction does not go to completion (a 100% yield on polycondensation is not obtained but a yield in excess of 90% is generally expected). Consequently, actual crosslinking is somewhat less than that theoretically possible or as credited herein to the various encapsulation wall formulations.

While both of said first and second intermediates can consist partially or entirely of polyfunctional reactants, as described above, whereby each reactant is able to crosslink with a complimentary crosslinking group on an adjacent polymer chain to obtain what may be termed a polycondensate wall which can be up to 200% crosslinked, it is preferred that only one of said first and second intermediates contain up to 100 percent of said polyfunctional reactant (100% crosslinked). In a more preferred embodiment of this invention, the capsule wall polymer is prepared with a polyfunctional crosslinking reactant replacing from 25 to 100% of a difunctional reactant (25–100% crosslinked).

Examples of suitable diamine and polyamine reactants to form the polyamide-polyurea, polyurea or polyamide capsule wall are ethylene diamine, phenylene diamine, toluene diamine, hexamethylene diamine, diethylene triamine, piperazine, 1,3,5-benzenetriamine trihydrochloride, 2,4,6-triaminotoluene trihydrochloride, tetraethylene pentamine, pentaethylene hexamine, polyethyleneamine, 1,3,6,-triaminonaphthalene and 3,4,5,8- tetraaminoanthroquinone. Examples of difunctional and polyfunctional acid-derived compounds providing —COCl and —SO$_2$Cl reactive groups are sebacoyl chloride, ethylene-bischloroformate, phosgene, azelaoyl chloride, adipoyl chloride, terephthaloyl chloride, dodecanedioic acid chloride, dimer acid chloride, 1,3-benzene tetra-acid chloride and 1,2,5-benezene trischloroformate. Intermediates useful in providing reactive isocyanate groups are represented by such compounds as paraphenylene diisocyanate, meta-phenylene diisocyanate, naphthalene-1,5-diisocyanate, 2,6-toluene diisocyanate, 4,4-diphenyl diisocyanate, the dichloro diphenyl methane diisocyanates, bibenzyl diisocyanate, bitolylene diisocyanate, the diphenyl ether diisocyanates, the dimethyldiphenyl diisocyanates, the polymethylene polyphenylisocyanates, triphenylmethane-4,4',4"-triisocyanate, isopropyl benzene diisocyanate and the like.

More specifically and preferably, the microencapsulation procedure is carried out by mixing the phytotoxic fungicide with a solvent to form a concentrated solution. The diacid chloride and the polyfunctional crosslinking reactant are added to the fungicide solution to provide a complete organic mix. The organic mix is poured into an aqueous solution of a dispersing agent, e.g., polyvinyl alcohol, while mechanically stirring the solution at high speed (8,000–15,000 rpm). This procedure forms droplets of the organic mix dispersed in the aqueous solution. The droplet size, and ultimate size of the microcapsule, is controlled by the mixer speed. The difunctional amine and either an acid or base for pH control, if needed, is then added to the aqueous solution while agitation is continued at the same high speed as mentioned above to form a slurry in which microcapsule walls begin to form about the droplets by interfacial polycondensation. About 30–60 seconds after the amine addition, the stirrer speed is reduced to about 1000 rpm and stirring is continued at this speed. After several hours of low speed stirring, the resulting suspension may be neutralized and passed through a 50 mesh screen (U.S. Series Designation, Standard Sieve Opening of 300 microns) to remove oversize particles. The screened suspension should contain microcapsules averaging from about 7 to about 25 microns in diameter. Some of the water in the suspension may be removed by decantation and the resulting mixture thickened with a sufficient amount of suspending agent, for example xanthan gum, to prevent settling.

An exemplary recipe for forming the polycondensate capsule wall about the organic solvent solution of TCMTB or related compound is as follows: Polyfunctional isocyanate, e.g., polymethylene polyphenylisocyanate (PAPI TM), x moles, where x equals 0 to 1; Diacid chloride, e.g., sebacoyl dichloride or difunctional isocyanate, e.g, toluene diisocyanate, 1−x moles; Difunctional amine, e.g., ethylene diamine, n−y moles, where n equals 1 to 3; difunctional polyamine, e.g., diethylene triamine, y moles, where y=0 to 1.5; in addition, a base such as sodium hydroxide may be included in the recipe to neutralize hydrochloric acid generated during the polycondensation reaction. Excess amine may be present in the recipe. The diacid chloride and/or isocyanate are added to the TCMTB solution which acts as a water-insoluble organic solvent, this organic mixture is dispersed in water and the amine is charged to the reaction as an aqueous solution.

MICROCAPSULE SUSPENSIONS

A suspension or slurry of the microcapsules in water at a concentration of active ingredient of from about 15–30% preferably 20–25%, based on the weight of the suspension, is the usual embodment for storage and shipping. This suspension of microencapsulated fungicide may have incorporated therein suspending agents, for example, crosslinked acrylic acid interpolymers as disclosed in U.S. Pat. No. 3,426,004; xanthan gum as disclosed in U.S. Pat. No. 4,107,191; hydroxyethyl cellulose, gums, clays, submicron-size silica, and other inorganic materials; and wetting agents and dispersants including polyvinyl alcohol, gelatin, methyl cellulose, casein, clays and various detergents.

To provide an aqueous dispersion or suspension of microencapsules capable of spray application, the thick, concentrated (15-30%) dispersion mentioned above is diluted by the applicator with water to the point where it can be readily sprayed with equipment used for aerial or ground application. A less dilute preparation is the choice for aerial application since less water and more active ingredient is transported. In general, dilution of the concentrate with water is sufficient to avoid clogging of conventional spray nozzles but less than that which will deter adequate coverage in one pass by the applicator. The dispersion of microcapsules as applied, will, for example, range in concentration from about 1 to 12% active ingredient (fungicide compound), based on the weight of the dispersion, or about 0.1 to about 1.0 pound of active ingredient per gallon. The applicator preferably applies this diluted dispersion at the rate of from about 0.15 to about 2.0 pounds, more preferably about 0.25 to 1.0 pound of active ingredient per acre.

MICROCAPSULE PARTICLE SIZE

The average particle size range of the microcapsules of this invention is critical. At particle sizes below the range, the area coverage of the capsules increases to the point that phytotoxicity will not be diminished below that of the unencapsulated fungicide. At particle sizes above the given range the area coverage is very low resulting in reduced phytotoxicity but much decreased fungicidal activity. Consequently, the average particle size of the microcapsules in the aqueous dispersion of this invention will be at least 5 microns and will not exceed about 50 microns in diameter. The preferred average particle size of the microcapsules is from about 7 to about 25 microns in order to provide the most effective fungicide control without increasing phytotoxicity. The size of the microcapsules is controlled during the process of encapsulation by using mixing, stirring or agitating means at a suitable rate of speed to form droplets of the to-be-encapsulated ingredients which are of the size or slightly smaller than the desired size of the resulting microcapsules, as previously explained.

The particle size of the microcapsules of this invention are measured either by using a microscope with a calibrated reticle and visually estimating the average particle size, or the size can be determined using a Coulter Counter. Microscopic determination generally is within ±5 microns of that size measured by the Coulter Counter. The Coulter Counter determines by electronic means the particle size distribution of the particles making up a test sample. From this distribution, $d_{16}$, $d_{50}$ and $d_{84}$ values are determined. These values are selected because they produce a convenient straight line in a log probability plot. $d_{16}$ represents the size (diameter in microns) which 16 weight percent of the capsules in the sample are equal to or larger than, $d_{50}$ represent the size which 50 weight percent of the capsules are equal to or larger than, and $d_{84}$ represents the size which 84 weight percent of the capsules are equal to or larger than.

WALL WEIGHT

The weight of the walls of the capsules of this invention is critical. If the proportion of wall to fungicidal composition is too great, the rate of release of the fungicide will be so slow as to be ineffective. Furthermore, too heavy a wall reduces the payload of the fungicidal product and will make it too expensive. If the proportion of the wall weight to the fungicidal component is too light, the rate of release will be too great and the protection against phytotoxicity will be lost. The wall weight, as a percent of the total weight of the microcapsules (combined weight of walls and fungicide composition), is calculated from the amount of ingredients in the recipe for preparing the encapsulated product and assumes that the reactants chemically unite to the degree of 100% of that theoretically possible. The calculated amount may be checked by removing the water from the microcapsule dispersion, drying the capsules and weighing the dried capsules. The solvent and active ingredient in the capsule are then removed by extraction and the empty capsules reweighed.

The broad range for the capsule wall weight is from about 5 to about 40%, based on the weight of the microcapsules. It is preferred that the wall be at least 10% and no greater than about 30% since it is more difficult to obtain the proper release rate with walls which are lighter than about 10%, but, it is most economical to use a wall of low weight as the capsule payload will be high i.e., each capsule will contain a high amount of active ingredient.

In general, the microencapsulated fungicide of this invention can be used on a variety of agricultural crops for foliar and/or soil applications including, but not limited to: grapes, cereals, soybeans and other beans, sugar beets, cotton, onions, potatoes, corn, tomatoes, citrus, cucurbits, sorghum, apples, avocados, and alfalfa for the control of disease such as: *Alternaria tenuis, Alternaria solani, Aspergillus nidulans, Aspergillus niger, Chaetomium globosum, Colletotrichum gossypii, Diaphorte citri, Elsinoe fawcetti,* Fusarium spp., *Fusarium oxysporum, Fusarium roseum, Fusiscladium effusum, Helminthosporium maydis, Helminthosporium oryzac, Monilinia fructicola, Penicillium roqueforti, Phoma betae, Phytophthora palmivora, Puccinia carthami, Puccinia coronata, Pythium aphanidermatum, Pythium debaryanum, Pythium ultimum, Rhizoctonia solani, Rhizopus stolonifer, Sclerotium rolfsii, Sphacelothca sorgi, Thielaviopsis basicola, Thielaviopsis paradoxa,* Tilletia supp., *Ustilago avenac, Ustilago hordei, Ustilago nuda, Venturia inaequalis, Verticillium alboatrum, Verticillium theobromae, Xanthomonas citri, Xanthomonas phaseoli, Colletotrichum gloeosporioides, Phytophtora nicotianae, Phytium aohani, Phomopsis citri, Verticillium dahliae, Helminthosporium teres, Puccinia striiformis, Pythium ultimum,* and *Piracaloria oryzae* as well as certain neuratodes (Meloidoggne spp.) and Mites (*Tetranychus orticae*).

EXAMPLES

The following examples are provided to demonstrate this invention. In the examples TCMTB [2-(thiocyanomethylthio) benzothiazole], a phytotoxic fungicide previously used for seed treatment, is employed as the material to be encapsulated and is representative of other phytotoxic fungicides of this invention.

Preparation of microencapsulated TCMTB 10/90, i.e., where the weight percent of the microcapsule wall, based on the total weight of the microencapsulated TCMTB, is 10% and the degree of crosslinking of the polyamide-polyurea microcapsule wall is 90%, is as follows:

Solutions A and B, identified below, are prepared by simple mixing.

| A |
|---|
| 50 g TCMTB (65% TCMTB in xylene) |
| 0.42 g sebacoyl chloride |
| 4.16 g polymethylene polyphenylisocyanate (PAPI ™) |

| B |
|---|
| 1.04 g ethylene diamine |
| 1.19 g diethylene triamine |
| 0.28 g NaOH (50 wt. %) |
| 25.0 g H$_2$O |

Solution A is added to 200 g of an aqueous solution (0.25 wt. %) of polyvinyl alcohol (Gelvatol ™) and the mixture emulsified for 30 seconds by mechanical stirrer (Kraft Model S-30) rotating at 9000 rpm. The emulsified mix is then added with stirring at the above speed to Solution B and, after the complete addition, stirring is continued for one hour at reduced speed (1000 rpm). Thereafter, the pH of the mixture is adjusted to 6–6.5 using concentrated hydrochloric acid. The product is sieved through a 50 mesh screen to remove oversized particles and then thickened with 0.3% (of total weight) of xanthan gum (Kelzan ™) to provide a stabilized product.

The preparation of microencapsulated TCMTB 10/50 with a polyamide-polyurea wall proceeds as described above for the microencapsulated TCMTB 10/90 except that the high speed mechanical stirring is at 9500 rpm, the pH is adjusted to about 7.0 and Solutions A and B of the following recipe are used.

| A |
|---|
| 50 g TCMTB (80% TCMTB in xylene) |
| 2.37 g sebacoyl chloride |
| 2.65 g polymethylene polyphenylisocyanate |

| B |
|---|
| 1.19 g ethylene diamine |
| 1.36 g diethylene triamine |
| 1.55 g NaOH (50 wt. %) |
| 20 g H$_2$O |

The preparation of microencapsulated TCMTB 10/100 with a polyurea wall proceeds as described for the above identified products except that Solutions A and B are as follows:

| A |
|---|
| 50 g of TCMTB (80 wt. % in xylene) |
| 4.47 g of polymethylene polyphenylisocyanate |

| B |
|---|
| 1.0 g ethylene diamine |
| 1.15 g diethylene triamine |
| 20 g H$_2$O |

The above preparations provide aqueous formulations of microencapsulated TCMTB with about 20 weight % active ingredient. Microcapsules of varying wall weights can be prepared by varying the proportions of acid chloride and/or crosslinking agent in Solution A. For example, to lower the percent of wall weight relative to the total weight of the microencapsulated fungicide, one uses less sebacoyl chloride and/or less polymethylene polyphenylisocyanate in the above described Solutions A.

The initial evaluation of the phytotoxicity of various microencapsulated TCMTB formulations was obtained in screening tests in the greenhouse on young soybean and wheat plants and is reported in Table 1. The rate of application was 12 ml. of a slurry of microcapsules or emulsifiable concentrate (EC), wherein the concentration of the active ingredient (TCMTB) was 815 parts by weight per million parts of slurry, sprayed to runoff of the young plants. The results demonstrate the substantial reduction in phytotoxicity when compared to the emulsifiable concentrate of TCMTB applied at the same rate.

TABLE 1

| Formulation | | | Phytotoxicity Rating* | |
|---|---|---|---|---|
| No. | % Wall | % Crosslinking** | Soybean | Wheat |
| 1 | 5 | 50 | 5 | 1 |
| 2 | 5 | 100 | 3 | 0 |
| 3 | 10 | 50 | 4 | 0 |
| 4 | 10 | 70 | 2 | 0 |
| 5 | 10 | 90 | 2 | 0 |
| 6 | 10 | 100 | 1 | 0 |
| EC | | | 7 | 1 |

*Ratings were taken 8 days after application based on the following scale:
0 = Normal
1 = Slight mottling
2 = Moderate mottling
3 = Severe mottling
4 = Slight desiccation
5 = Moderate desiccation
6 = Severe desiccation
7 = Slight defoliation
8 = Moderate defoliation
9 = Severe defoliation
10 = Plant necrosis
**% crosslinking of resinous polycondensate wall. 100% crosslinking indicates complete replacement of acid chloride reactant thereby forming a polyurea capsule wall.

Two of the formulations of Table 1 were also tested in the field against apple scab (*Venturia inaequalis*) on apple trees at the rate of 100 gallons per acre. The application of the formulations to the trees were made beginning on April 18 and repeated on April 30, May 13, May 24, June 21 and July 30. Results of this testing is shown in Table II.

TABLE II

| Formulation No. | Conc.* | % Control** | Phytotoxicity-% Reduction+ |
|---|---|---|---|
| EC | 0.33 | — | — |
|  | 0.90 | — | — |
| 3 | 0.33 | 74 | 69 |
|  | 0.90 | 76 | 90 |
| 5 | 0.33 | 72 | 81 |
|  | 0.90 | 77 | 83 |

*Pounds of active ingredient (TCMTB) per 100 gal. of spray.
**Treatment with EC was discontinued because of extreme phytotoxicity which threatened to kill apple trees.
+Percent reduction of phytotoxicity from microencapsulated fungicide versus EC.

Table III shows the results of testing of Formulation No. 3 of Tables I and II in the field against phytophthora blight on pepper plants.

TABLE III

| Formulation | Rate* | % Blight** | Yield (bushels/acre) |
|---|---|---|---|
| No. 3 | 0.25 | 3.8–7.7 | 271.3 |
| Ridomil 2E ™ + | 0.50 | 7.7–7.7 | 244.3 |
| Check | — | 25.0–28.9 | 209.2 |

*Pounds of active ingredient per acre; three applications at three week intervals.
**Visual observations made at two week interval (Aug. 23 and Sept 5)
+Reported to be N-(2,6-dimethylphenyl)-N-(methoxyacetyl)-alanine methyl ester - a commerically available fungicide.

Similar good results were obtained with microencapsulated TCMTB formulations when used as a spray on squash and cucumbers for the control of powdery mildew and anthracnose.

We claim:

1. A fungicide product comprising microcapsules containing a phytotoxic compound of the formula:

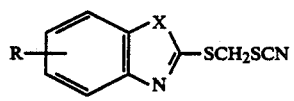

where X is —O— or —S— and R is alkyl, alkoxy, alkylamino, halo, nitro or hydrogen wherein the alkyl group or radical has from 1 to 6 carbon atoms, said microcapsules having walls of a resinous polycondensate selected from the group consisting of crosslinked polyurea, crosslinked polyamide and crosslinked polyamide-polyurea wherein the degree of crosslinking ranges from about 25 to 100%, said walls being about 10 to about 30% of the total weight of said microcapsules, and said microcapsules having an average size ranging from about 7 to about 25 microns in diameter.

2. The fungicide product of claim 1 wherein the phytotoxic compound is dissolved or suspended in a water-immiscible solvent at a concentration of said compound in excess of 60% based on the total weight of the compound and solvent.

3. The fungicide product of claim 2 wherein said compound is 2-(thiocyanomethylthio) benzothiazole.

4. The fungicidal product of claim 3 wherein said resinous polycondensate is crosslinked polyamide-polyurea.

5. The fungicide product of claim 1 wherein said compound is 2-(thiocyanomethylthio) benzothiazole.

6. The fungicidal product of claim 1 wherein said resinous polycondensate is crosslinked polyamide-polyurea.

7. The fungicidal product of claim 1 wherein said microcapsules are suspended in an aqueous medium at a concentration of phytotoxic compound ranging from about 1 to about 30% based on the weight of aqueous microcapsule suspension.

8. The fungicide product of claim 7 wherein said aqueous medium contains from about 0.15 to about 0.5% of xanthan gum based on the weight of the aqueous microcapsule suspension.

9. The fungicidal product of claim 8 wherein said resinous polycondensate is crosslinked polyamide-polyurea.

10. The fungicide product of claim 9 wherein said compound is 2-(thiocyanomethylthio) benzothiazole.

11. The fungicidal product of claim 10 wherein the concentration of benzothiazole in said aqueous medium ranges from about 15 to about 30%.

12. The fungicide product of claim 10 wherein the concentration of benzothiazole in said aqueous medium ranges from about 1 to about 12%.

13. A process of treating fungal disease on growing plants which comprises applying to said plants an aqueous suspension of microcapsules containing a phytotoxic compound having the following formula:

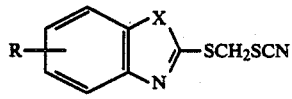

where X is —O— or —S— and R is alkyl, alkoxy, alkylamino, halo, nitro or hydrogen wherein the alkyl group or radical has from 1 to 6 carbon atoms, at a rate of from 0.15 to about 2.0 pound of phytotoxic compound per acre, said microcapsules having walls of a resinous polycondensate selected from the group consisting of crosslinked polyurea, crosslinked polyamide and crosslinked polyamide-polyurea wherein the degree of crosslinking ranges from about 25 to 100%, said walls being from about 10 to about 30% of the total weight of said microcapsules, and said microcapsules having an average size ranging from about 7 to about 25 microns in diameter.

14. The process of claim 13 wherein said compound is 2-(thiocyanomethylthio) benzothiazole.

15. The process of claim 14 wherein said compound is dissolved or suspended in a water-immiscible solvent.

16. The process of claim 15 wherein the microcapsule wall is crosslinked polyamide-polyurea.

17. The process of claim 15 wherein the rate of application is from about 0.25 to about 1.0 pound of phytotoxic compound per acre.

* * * * *